US011173096B2

(12) United States Patent
Nicolas et al.

(10) Patent No.: US 11,173,096 B2
(45) Date of Patent: Nov. 16, 2021

(54) PACKAGING DEVICE CONFIGURED TO SUPPORT MEDICAL CONTAINERS AND METHOD FOR REMOVING THE MEDICAL CONTAINERS FROM SAID PACKAGING DEVICE

(71) Applicant: Becton Dickinson France, Le Pont de Claix (FR)

(72) Inventors: Maxime Nicolas, Grenoble (FR); Gwenn le Dimet, Charavines (FR); Julien Gagliano, Grenoble (FR); Rémi Jamon, Vaulnaveys le Haut (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 16/651,845

(22) PCT Filed: Oct. 2, 2018

(86) PCT No.: PCT/EP2018/076747
§ 371 (c)(1),
(2) Date: Mar. 27, 2020

(87) PCT Pub. No.: WO2019/068688
PCT Pub. Date: Apr. 11, 2019

(65) Prior Publication Data
US 2020/0246223 A1 Aug. 6, 2020

(30) Foreign Application Priority Data
Oct. 2, 2017 (EP) .................................... 17306312

(51) Int. Cl.
*A61J 1/16* (2006.01)
*A61M 5/00* (2006.01)
*B65D 25/10* (2006.01)

(52) U.S. Cl.
CPC ................. *A61J 1/16* (2013.01); *A61M 5/008* (2013.01); *B65D 25/108* (2013.01); *A61M 2209/084* (2013.01)

(58) Field of Classification Search
CPC .... A61J 1/14; A61J 1/16; A61M 5/00; A61M 5/008; A61M 5/31; A61M 2209/084; B65D 21/00; B65D 25/10; B65D 25/108
(Continued)

(56) References Cited

U.S. PATENT DOCUMENTS 9,718,583 B2 * 8/2017 Nicoletti .............. B65D 25/108
10,023,358 B2 * 7/2018 Carrel ................... A61M 5/008

FOREIGN PATENT DOCUMENTS

DE        7307208 U    5/1973
DE        3506218 A1   8/1986
(Continued)

*Primary Examiner* — Bryon P Gehman
(74) *Attorney, Agent, or Firm* — The Webb Law Firm

(57) ABSTRACT

This packaging device comprises a first stage (2a) of supporting units (20) configured to support a first plurality of medical containers (100a) in a first plane, a second stage (2b) of supporting units (20) configured to support a second plurality of medical containers (100b) in a second plane parallel to said first plane, the first plane and the second plane being spaced apart from each other so that the distal ends (106) of the first plurality of medical containers (100a) extend between medical containers of the second plurality of medical containers (100b), and the supporting units (20) of the first and second stages (2a, 2b) being configured so that the medical containers of the first and second pluralities of medical containers (100a, 100b) are oriented in a same direction. The first stage (2a) of supporting units (20) is formed by a first plate-shaped nest and the second stage (2b) of supporting units (20) is formed by a second plate-shaped nest.

15 Claims, 4 Drawing Sheets

(58) Field of Classification Search
USPC .......................................................... 206/364
See application file for complete search history.

(56) References Cited

FOREIGN PATENT DOCUMENTS

| EP | 0452751 A1 | 10/1991 |
| EP | 2119463 A1 | 11/2009 |
| WO | 2012042291 A1 | 4/2012 |

\* cited by examiner

PACKAGING DEVICE CONFIGURED TO SUPPORT MEDICAL CONTAINERS AND METHOD FOR REMOVING THE MEDICAL CONTAINERS FROM SAID PACKAGING DEVICE

CROSS-REFERENCE TO RELATED APPLICATIONS

This application is the United States national phase of International Application No. PCT/EP2018/076747 filed Oct. 2, 2018, and claims priority to European Patent Application No. 17306312.4 filed Oct. 2, 2017, the disclosures of which are hereby incorporated by reference in their entirety.

BACKGROUND OF THE INVENTION

Field of the Invention

The present invention relates to a packaging device for containing a plurality of medical containers and a method for removing the plurality of medical containers from this packaging device.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a container contained in the packaging device of the invention, and the "proximal direction" is to be understood as meaning the opposite direction to said direction of injection, that is to say the direction towards the user's hand holding a container as for an injection operation.

Description of Related Art

Medical containers, such as pre-fillable or prefilled syringes, often need to be transported from one site to another site, for instance from a manufacturing site to a second site where the medical containers may be filled with an agent, such as a vaccine, a medicine or a therapeutic agent. Less frequently, the medical containers may be manufactured and filled in the same first site and then be transported to a storage site. During transportation, the medical containers are usually put into a global packaging, this global packaging comprising a nest supporting the medical containers, a housing or tub containing the nest, a sealing cover closing the tub, and a so-called header bag ensuring sterility.

The nest is a plate-shaped tray that is generally configured to support more than one hundred medical containers. The nest is placed inside the box-shaped tub or housing which has one opening sealed by the sealing cover. The box-shaped housing or tub provides a simple and efficient storage and transportation solution for a plurality of medical containers. Removal of the nest holding the medical containers from the tub just requires removal of the sealing cover and extraction of the plate-shaped nest from the tub by translating this nest through the opening of the tub. This process has the advantage of being simple and thus requires limited equipment.

There is however a constant need to limit the storage or transportation costs. Besides, there is a need not to complicate the removal of the medical containers.

SUMMARY OF THE INVENTION

An aspect of the invention is a packaging device configured to contain a plurality of medical containers, said packaging device allowing storage and transportation costs reduction.

An aspect of the invention is a packaging device configured to support medical containers, the packaging device comprising a first stage of supporting units configured to support a first plurality of medical containers in a first plane, a second stage of supporting units configured to support a second plurality of medical containers in a second plane parallel to said first plane, the first plane and the second plane being spaced apart from each other so that the distal ends of the first plurality of medical containers extend between medical containers of the second plurality of medical containers, and the supporting units of the first and second stages being configured so that the medical containers of the first and second pluralities of medical containers are oriented in a same direction.

This two-stage packaging device enables to increase the number of medical containers per volume unit and thus decreases the storage and transportation costs. Besides, having the two pluralities of medical containers oriented in the same direction provides easy removal of the medical containers without high equipment investments.

In embodiments, the supporting units of the first stage and the supporting units of the second stage are configured so that the first plurality of medical containers and the second plurality of medical containers are arranged in staggered rows relative to each other.

Having medical containers of the first plurality of medical containers which are in quincunx with respect to the medical containers of the second plurality of medical containers enables to reduce the volume of the packaging device, and therefore to limit the storage and transportation costs.

In embodiments, the first stage of supporting units is configured to support a proximal end of the first plurality of medical containers and the second stage of supporting units comprises a lateral blocking surface configured to prevent radial movement of the distal ends of the first plurality of medical containers.

This limits the risks of impacts between adjacent medical containers, while limiting the volume occupied by the medical containers, and therefore limiting the volume of the packaging device.

In embodiments, the first stage of supporting units comprises a maintaining surface configured to prevent the second plurality of medical containers from leaving the second stage of supporting units.

This enables to prevent a fall and breakage of a medical container inside the packaging device during transportation.

In embodiments, the first stage of supporting units is formed by a first plate-shaped nest and the second stage of supporting units is formed by a second plate-shaped nest.

This provides a cost effective solution to transport and store the two pluralities of medical containers.

In embodiments, the packaging device comprises a strut element removably attached to the first and second stages of supporting units so as to fix together the first and second stages of supporting units.

As a result, the two pluralities of medical containers may be handled together. This allows a quick insertion or removal of the medical containers inside or outside the packaging device.

In embodiments, the supporting units of the first and second stages respectively delimit first and second apertures, each first aperture being configured to receive one medical container of said first plurality of medical containers and each second aperture being configured to receive one medical container of said second plurality of medical containers.

This provides a quick insertion or removal of the medical containers inside or outside the packaging device.

In embodiments, the supporting units of the first and second stages respectively comprise first and second axial stops, each of the first axial stop being configured to support a flange of a medical container of said first plurality of medical containers, and each of the second axial stop being configured to support a flange of a medical container of said second plurality of medical containers.

This is a cost effective solution to support the medical containers without increasing the packaging device volume.

In embodiments, the supporting units of the first and second stages respectively comprise first and second guiding conduits configured to prevent radial movements of the first and second pluralities of medical containers.

This limits the movements of the medical containers relative to the supporting units to a translational movement such as an axial movement. The medical containers are therefore supported in a more stable way.

In embodiments, the packaging device comprises a housing containing the first and second stages of supporting units, said housing delimiting an opening configured to allow insertion or removal of the first and second stages together inside or outside the housing.

As a result, one opening enables to insert or remove all the medical containers as a whole.

Another aspect of the invention is a method for removing the pluralities of medical containers from a packaging device as above described, comprising the step of removing the first stage of supporting units together with the second stage of supporting units.

As a result, this method allows fast removal of a high number of medical containers.

In embodiments, the method further comprises the step of separating the first and second stages of supporting units from each other.

This allows handling the first and second stages and pluralities of medical containers separately. This step may be performed by removal of the strut element.

The method may further comprise an inspection step of the first and/or second plurality of medical containers.

The method may comprise the step of removing the first plurality of medical containers from the first stage of supporting units and/or removing the second plurality of medical containers from the second stage of supporting units. This removing step preferably occurs after the separation step of the first and second stages of supporting units.

BRIEF DESCRIPTION OF THE DRAWINGS

The invention and the advantages arising therefrom will clearly emerge from the detailed description that is given below with reference to the appended drawings as follows.

DESCRIPTION OF THE INVENTION

With reference to FIGS. 1 to 7 is shown a packaging device 1 of the invention. The packaging device 1 of the invention is intended to contain a plurality of medical containers 100. The medical containers 100 may be vials or preferably syringes, such as pre-fillable or prefilled syringes. The medical containers 100 are intended, after filling, to contain a medical agent such as a vaccine, a medicine or a therapeutic agent.

Figure 5:
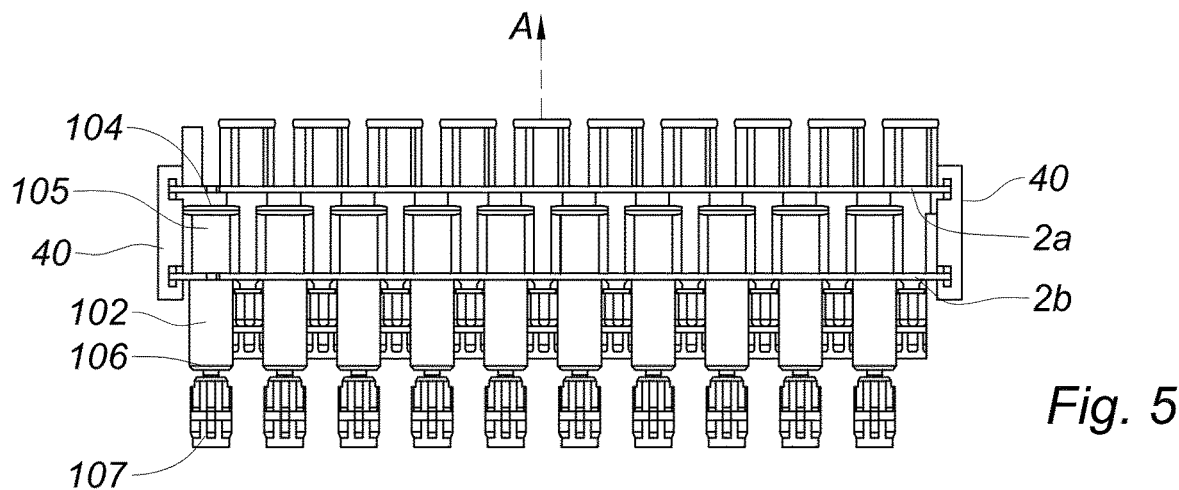
FIG. 5 is a side view of the first and second stages of supporting units of a packaging device according to an embodiment of the invention.
Figure 6:
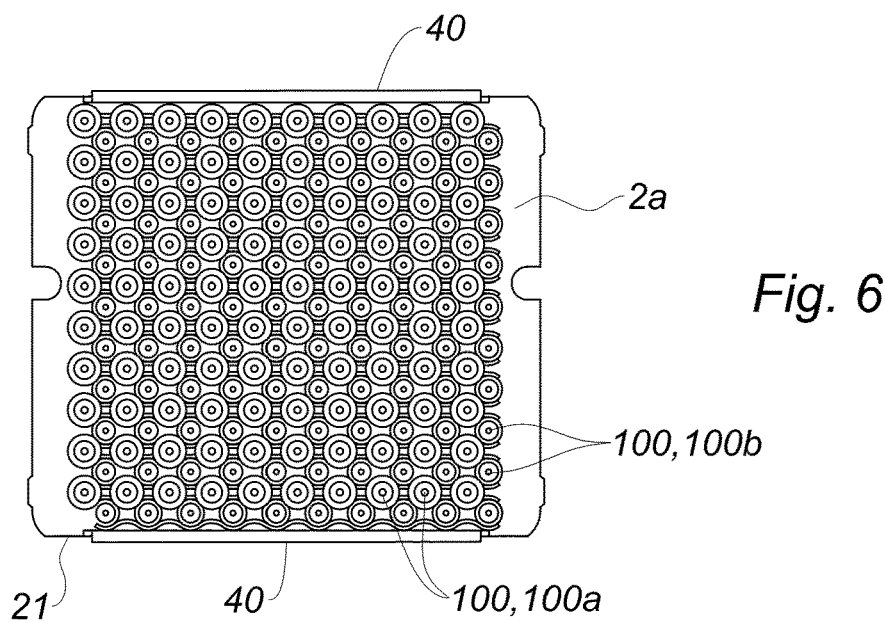
FIG. 6 is a top view of the first and second stages of supporting units of a packaging device according to an embodiment of the invention.

As shown on FIG. 5, the medical containers 100 typically comprise an elongated barrel 102 defining a reservoir for containing said vaccine, medicine or therapeutic agent. The tube-shaped barrel 102 may be cylindrical. The medical container 100 includes a flange 104 at a proximal end 105 of the barrel 102, and a tip closed by a needle and/or a cap 107 at a distal end 106 of the medical container 100.

With reference to FIGS. 4 to 7, the packaging device 1 is configured to support the medical containers 100 so that said medical containers 100 are arranged parallel to each other and to a longitudinal axis A.

The packaging device 1 comprises two stages 2a, 2b of supporting units 20: a first stage 2a configured to support a first plurality of medical containers 100a in a first plane orthogonal to said longitudinal axis A and a second stage 2b configured to support a second plurality of medical containers 100b in a second plane parallel to the first plane and distally away from the first plane. For example, each stage 2a, 2b may be configured to support at least 100 or 160 medical containers 100.

By a stage of supporting units configured to support medical containers in a plane it is meant that the proximal, respectively the distal, ends 105, 106 of the medical containers supported by this stage of supporting units are substantially positioned at a same level and thus are substantially contained in a same plane.

The first stage 2a and the second stage 2b are at a predetermined distance from each other so that the distal ends 106 of the medical containers 100a supported by the first stage 2a are located between at least two adjacent medical containers 100b supported by the second stage 2b. The first stage 2a and the second stage 2b may be spaced from each other so that at least one medical container 100a supported by the first stage 2a is inserted at least partially between at least two medical containers 100b, and preferably four medical containers 100b, supported by the second stage 2b.

Figure 7:
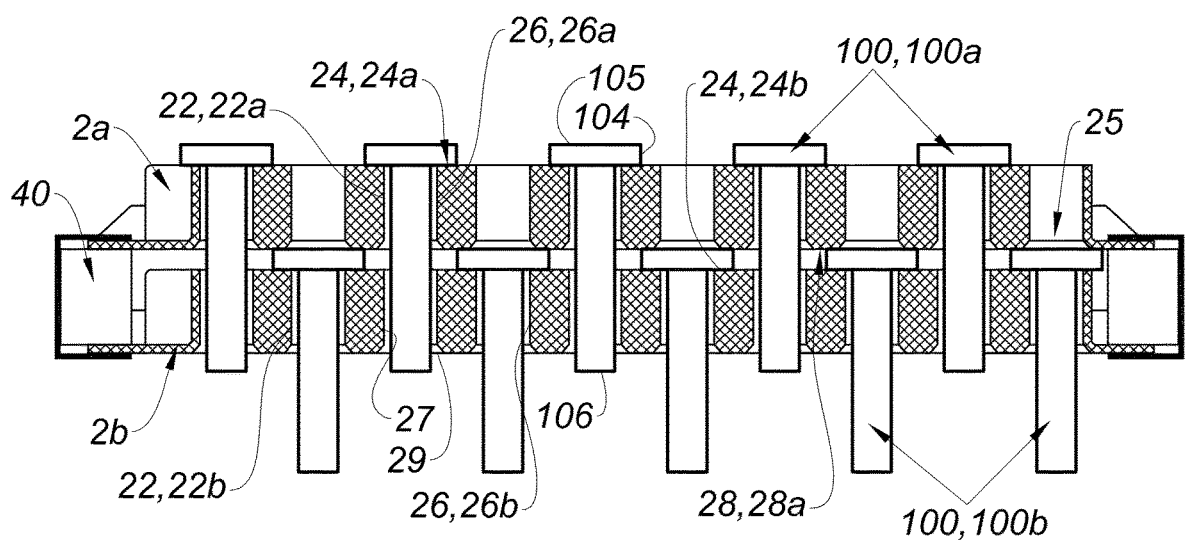
FIG. 7 is a schematic view of the first and second stages of supporting units of a packaging device according to an embodiment of the invention.

As shown for instance on FIG. 7, the distal ends 106 of the first medical containers 100a are located at a level comprised between the proximal ends 105 and the distal ends 106 of the second medical containers 100b preferably closer to their distal ends 106 than their proximal ends 105. This allows to store and transport a high number of medical containers 100 in a reduced volume.

Besides, the supporting units 20 of the first and second stages 2a, 2b are configured so that the medical containers 100a, 100b are oriented in a same direction with regard to axis A. This provides a simple handling of both the first and second pluralities of medical containers 100a, 100b.

The supporting units 20 of each stage 2a, 2b may be aligned according to parallel rows, so that the corresponding medical containers 100a, 100b are also arranged in parallel rows. Preferably, the supporting units 20 of the first stage 2a and the supporting units 20 of the second stage 2b are offset relative to each other. Therefore, the supporting units 20 of the first stage 2a do not face, are not aligned with the supporting units 20 of the second stage 2b with respect to the longitudinal axis A. This enables to store the medical containers in a lower volume.

In a preferred embodiment, the supporting units 20 of the first stage 2a and the supporting units 20 of the second stage 2b are arranged so that the medical containers 100a supported by the first stage 2a and the medical containers 100b supported by the second stage 2b are arranged in staggered rows relative to each other.

By medical containers 100a, 100b arranged in staggered rows, or quincunx, relative to each other, it is meant that between four adjacent medical containers 100a of the first plurality of medical containers 100 extends a medical container 100b of the second plurality of medical containers 100, and conversely between four adjacent medical containers 100b of the second plurality of medical containers 100 extends a medical container 100a of the first plurality of medical containers 100.

The supporting units 20 of both stages 2a, 2b are preferably configured so that the first plurality of medical containers 100a and the second plurality of medical containers 100b are removable from the packaging device 1 along the same direction with respect to the longitudinal axis A.

With reference to FIGS. 1 to 7, the packaging device 1 may comprise a housing 60 containing both the first and second stages 2a, 2b supporting the first plurality of medical containers 100a and the second plurality of medical containers 100b. The packaging device 1 may also comprise at least one, preferably two, strut element 40 which connects the first stage 2a and the second stage 2b. The packaging device 1 may also comprise at least one sealing element (not shown) configured to close the packaging device 1 in order to keep sterility of a volume configured to contain the medical containers 100.

The first stage 2a and the second stage 2b may be plate-shaped. For example, the first and second stages 2a, 2b may be two separate plate-shaped nests. A nest is a plate or tray provided with through-holes, hereinafter apertures 22, aligned according to predetermined rows, each hole being configured to receive the barrel of one medical container. These two stages 2a, 2b may be similar. The stages 2a, 2b may have a square or rectangular shape. The stages 2a, 2b have at least one, preferably two opposite, connecting sides 21, at least one, preferably two opposite, supporting sides 23. The stages 2a, 2b have a top face 25 and a bottom face 28.

The supporting units 20 of the first and second stages 2a, 2b may each comprise some or all of the following features: an aperture 22 configured to receive one of the medical containers 100a, 100b, an axial stop 24 configured to support the flange 104 of one of the medical containers 100a, 100b, and/or a guiding conduit 26 configured to prevent or at least limit radial movements of the medical container 100 supported by the supporting unit 20 so as to avoid collisions between adjacent medical containers 100.

The apertures 22 may be through-holes extending from the top face 25 to the bottom face 28 of the corresponding stage 2a, 2b. The apertures 22 and the medical containers 100 may have a complementary shape. The apertures 22 lead into the corresponding guiding conduit 26.

The axial stops 24 may be provided at a proximal end of the guiding conduits 26. The axial stops 24 may extend around the apertures 22. The axial stops 24 of the first stage 2a and the axial stops 24 of the second stage 2b may be spaced from each other so that the distal end 106 of a medical container of the first plurality of medical containers 100a is located between medical containers of the second plurality of medical containers 100b. The second axial stops 24b may be located at an intermediate portion of the first medical containers 100a, between the proximal end 105 and the distal ends 106 of the first medical containers 100a, preferably closer to the proximal ends 105 than the distal ends 106. The axial stops 24 of the first and second stages 2a, 2b are preferably oriented in the same way.

The guiding conduit 26 may be a guiding tube, such as a tubular sleeve or a lateral wall, said sleeve or lateral wall and the medical container 100 having a complementary shape, for example a cylindrical shape. The guiding conduit 26 is configured to maintain the proximal end 105 of the medical containers 100. The guiding conduit 26 extends around and along the longitudinal axis A. The guiding conduits 26 may protrude from the top face 25 of the corresponding stage 2a, 2b.

The flange 104 of the medical containers 100 may be designed to abut on a corresponding axial stop 24. In particular, the outer diameter of the flange 104 of the medical containers 100 is greater than the diameter of the guiding conduit 26 or reception aperture 22.

As visible on FIG. 7, the first stage 2a is configured to support a proximal end 105 of the first plurality of medical containers 100a, while the second stage 2b comprises a lateral blocking surface 27 configured to prevent or at least limit lateral movements of an intermediate portion or of the distal end 106 of the first plurality of medical containers 100a. The lateral blocking surface 27 may delimit an opening 29 extending through the second stage 2b. The openings 29 and the medical containers 100 may have a complementary shape. The openings 29 may face the apertures 22 of the first stage 2a. The openings 29 are preferably arranged in staggered rows with respect to the apertures 22 of the second stage 2b.

The first stage 2a may preferably comprise a maintaining surface 28a configured to prevent the second plurality of medical containers 100b from leaving the supporting units 20 of the second stage 2b. This maintaining surface 28a preferably corresponds to the bottom face 28 of the first stage 2a.

Figure 4:
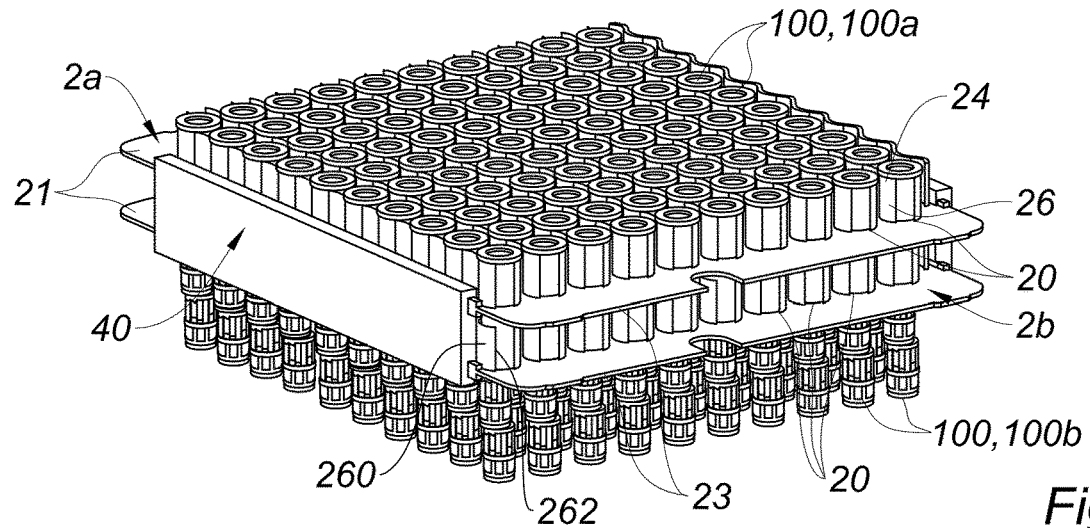
FIG. 4 is a perspective view of the first and second stages of supporting units of a packaging device according to an embodiment of the invention.

As shown on FIG. 4, the strut elements 40 are removably attached to the first stage 2a and to the second stage 2b. More precisely, each strut element 40 connects a connecting side 21 of the first stage 2a to a connecting side 21 of the second stage 2b. The strut element 40 maintains the predetermined distance between the first and second stages 2a, 2b. The strut element 40 also fixes the first and second stages 2a, 2b together so that the first and second stages 2a, 2b may be handled as a whole. The strut elements 40 may and the connecting sides 21 of the stages 2a, 2b may have a complementary shape, such as a complementary T-shape. For example, the strut elements 40 comprise a first groove 42a configured to fit the connecting side 21 of the first stage 2a and a second groove 42b configured to fit the connecting side 21 of the second stage 2b. In order to separate the first and second stages 2a, 2b, a user just needs to slide the strut elements 40 along an axis parallel to the connecting sides 21.

Figure 1:
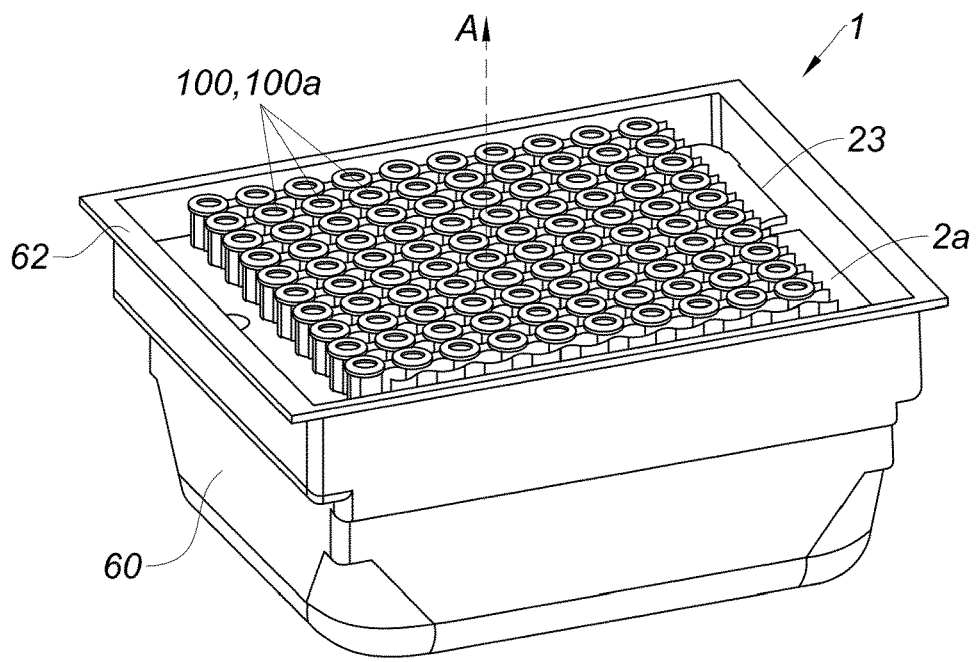
FIG. 1 is a perspective view of a packaging device according to an embodiment of the invention.
Figure 2:
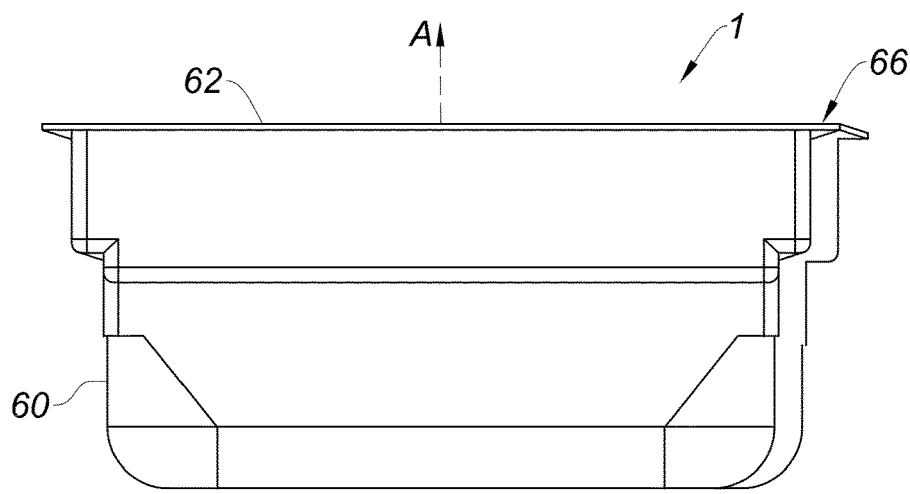
FIG. 2 is a side view of a packaging device according to an embodiment of the invention.
Figure 3:
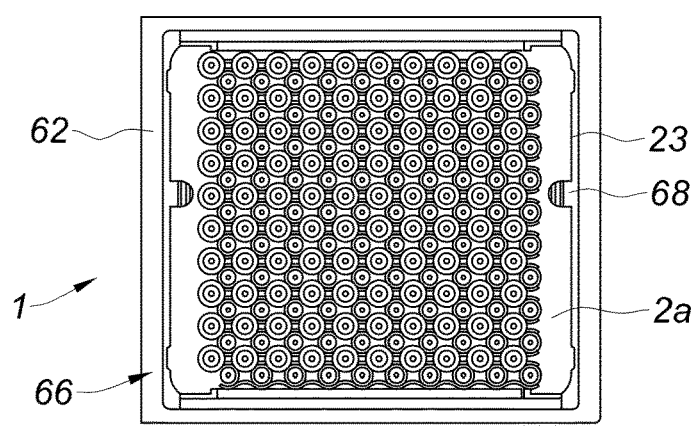
FIG. 3 is a top view of a packaging device according to an embodiment of the invention.

As shown on FIGS. 1 and 3, the housing 60 defines an internal storage volume configured to contain the two stages of supporting units 20 supporting the two pluralities of medical containers 100a, 100b.

The housing 60 delimits an opening 62 configured to allow insertion or removal of the first and second stages 2a, 2b together inside or outside the housing 60, by means of a translational movement of the first and second stages 2a, 2b along the longitudinal axis A with respect to the housing 60. The opening 62 thus leads into said internal volume 24. The opening 62 is preferably orthogonal to the longitudinal axis A. The opening 62 and the stages 2a, 2b may have a complementary shape, the opening 62 having dimensions greater than that of the stages 2a, 2b.

The housing 60 may comprise at least a shoulder 68, preferably two shoulders 68, configured to support one of the two stages 2a, 2b, more precisely at least a supporting side 23 of one of these two stages 2a, 2b.

The sealing element is configured to close the opening 62 so as to keep the internal volume sterilized. The sealing element may therefore comprise a microbial barrier. The sealing element may also be permeable to a sterilization gas, so that the interior of the packaging device 1 can be sterilized while the sealing element closes the opening 62. The sterilization gas may be for instance ethylene oxide (EO). For instance, the sealing element may comprise a Tyvek® sheet or any material that is airtight but permeable to a sterilization gas such as for example ethylene oxide. The sealing element is configured to be removed before removing the two stages 2a, 2b. The sealing element may be attached, for example glued or thermo-glued, onto an attachment surface 66 of the housing 60. The attachment surface 66 may extend around the opening 62.

A bottom face of the sealing element may be configured to prevent the first plurality of medical containers 100a from inadvertently leaving the supporting units 20 of the first stage 2a. Therefore, as long as the sealing element is hold in place, the sealing element permits to retain the first plurality of medical containers 100a inside the supporting units 20 of the first stage 2a.

The packaging device 1 may comprise a sealing bag (not shown) completely enclosing the housing 60. The sealing bag is configured to keep the internal volume sterilized. This sealing bag may form the sealing element. This sealing bag, or header bag, may comprise a material which is permeable to a sterilization gas, such as Tyvek®. The sealing bag may also be a plastic bag or a combination of both materials, plastic and permeable to gas sterilization.

Figure 8:
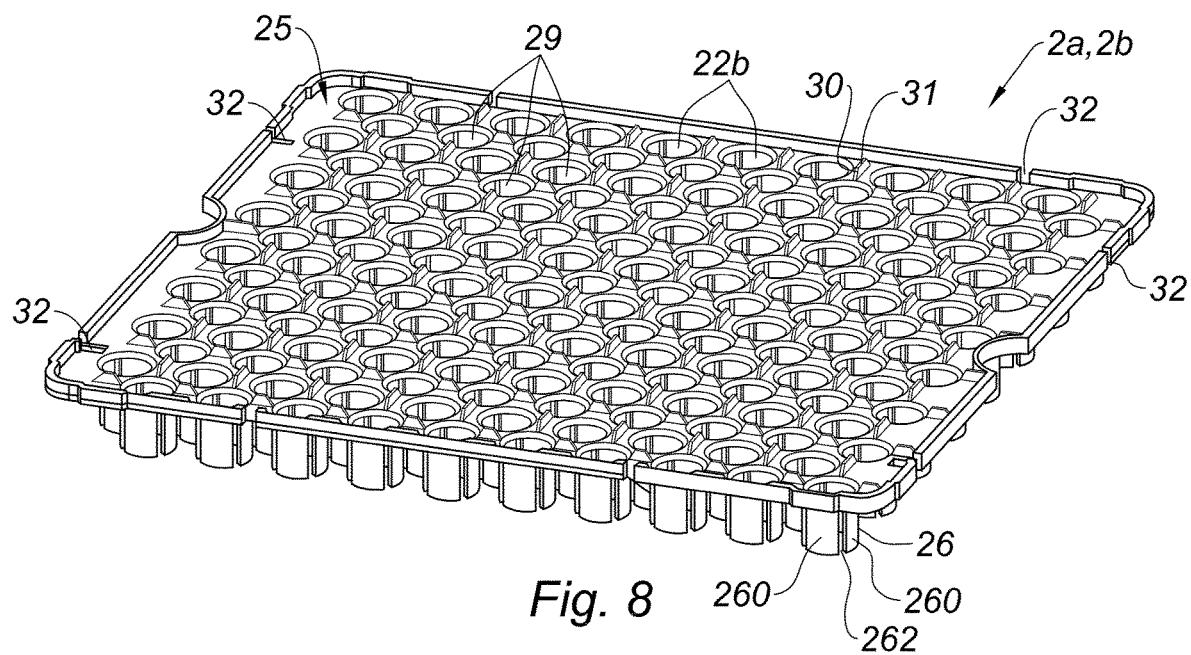
FIG. 8 is a perspective view of a nest of a packaging device according to an embodiment of the invention.
Figure 9:
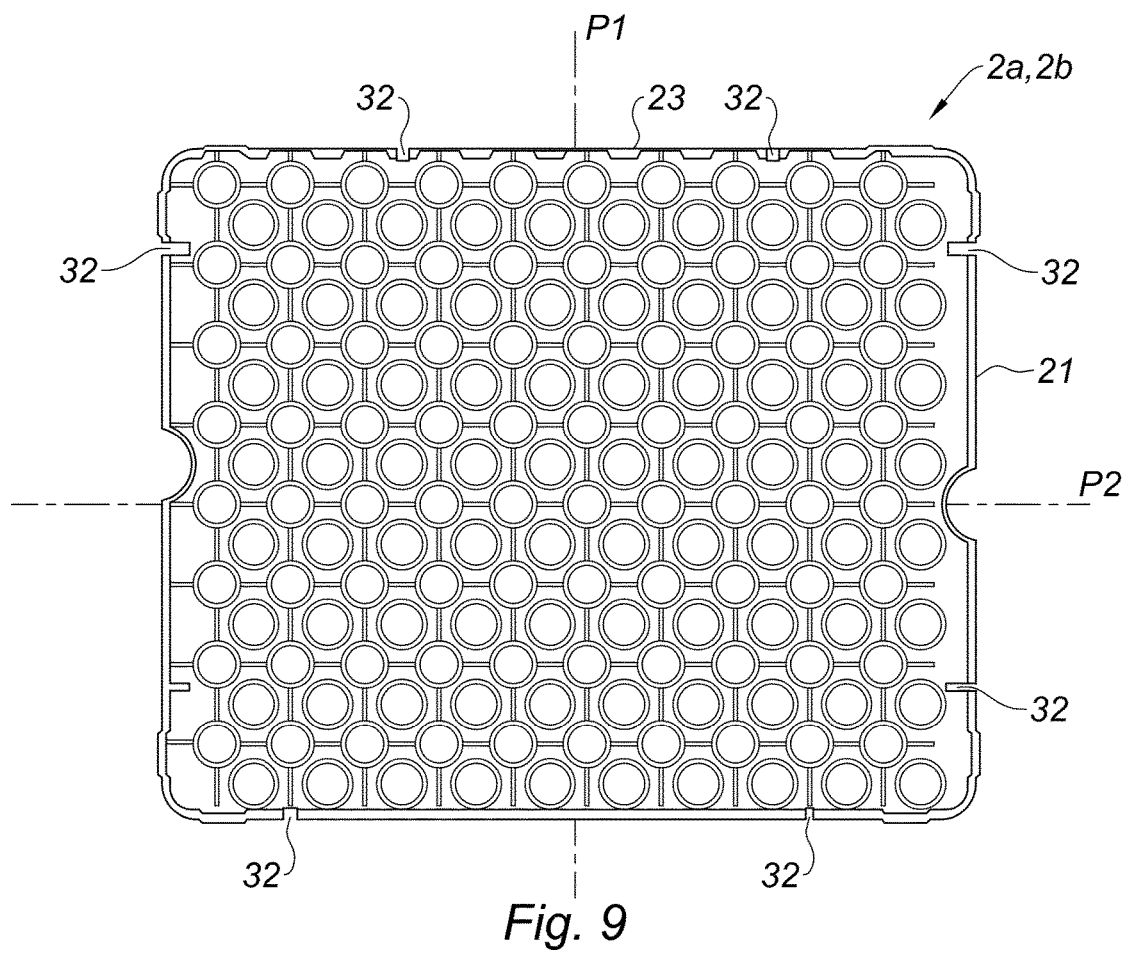
FIG. 9 is a top view of a nest of a packaging device according to an embodiment of the invention.

With reference to FIGS. 8 and 9 is shown a first or second stage 2a, 2b of a packaging device 1 according to another embodiment. The features which are similar to the above-described embodiments are designated by the same numeral references.

As shown on FIG. 8, the guiding conduit 26 may protrude from the bottom face 28 of the stage 2a, 2b, in order to allow a more compact storage.

Furthermore, as shown on FIGS. 1 and 8, the guiding conduits 26 may advantageously comprise at least two guiding tabs 260, a slit 262 being delimited between said at least two guiding tabs 260. This allows to reduce raw material costs and lighten the packaging device 1. The slits 262 extend along a direction orthogonal to the stage 2a, 2b. The slits 262 preferably extend along the whole length of the guiding conduit 26.

Advantageously, at least the second stage 2b may comprise slanted walls 30 configured to guide the distal end 107 of the medical containers 100 supported by the first stage 2a inside the openings 29 of said second stage 2b. The slanted walls 30 preferably protrude from the top face 25 of the second stage 2b, opposite the guiding conduits 26. The slanted walls 30 may be arranged at an end of a rib 31, so as to reduce material costs. The ribs 31 may be aligned in parallel rows so as to stiffen the second stage 2b. Both ends of said ribs 31 may be provided with a slanted wall 30. Besides, the ribs 31 preferably extend orthogonal to the corresponding stage 2a, 2b.

As visible on FIG. 9, the packaging device 1 may comprise keyed elements configured to allow a single predetermined positioning of the stages 2a, 2b inside the housing 60. The keyed elements may comprise slits 32 configured to engage ribs having a complementary shape. For example, one or several sides 21, 23 of the stages 2a, 2b are provided with the slits 32 while an internal wall of the housing 60 is provided with the complementary ribs. As visible on FIG. 9, the keyed slits 32 have different shapes or locations, so that the slits 32 are advantageously asymmetric with regard to a first vertical median plane P1 and/or to a second vertical median plane P2. The first vertical median plane P1 extends at the middle and orthogonally to the supporting sides 23, while the second median plane P2 extends at the middle and orthogonally to the connecting sides 21.

Another aspect of the invention is a method for removing the pluralities of medical containers 100a, 100b from a packaging device as above described. This method comprises the step of removing the first stage 2a of supporting units together with the second stage 2b of supporting units 20. The first and second stages 2a, 2b may be removed by means of a translational movement parallel to axis A. Removal of the first and second stages 2a, 2b is operated by passing the first and second stages 2a, 2b as a whole through the opening 62 of the housing 60.

Before removing the first and second stages 2a, 2b, the method may comprise a step of removing the sealing element closing the opening 62. This sealing element may be peeled off.

After having removed the two stages 2a, 2b from the housing 60, the method may comprise the step of separating the first and second stages 2a, 2b from each other. This step may comprise removing the at least one or the two strut elements 40 connecting the two stages 2a, 2b, for example by a sliding movement of the at least one or two strut elements 40 relative to the first and second stages 2a, 2b.

After having separated the first and second stages 4a, 4b, the method may further comprise an inspection step of the first and/or second plurality of medical containers 100a, 100b.

The method may further comprise the step of removing the first plurality of medical containers 100a from the first stage 4a of supporting units and/or removing the second plurality of medical containers 100b from the second stage 2b of supporting units. This step preferably occurs after the separation of the first and second stages 2a, 2b of supporting units 20.

The invention claimed is:

1. A packaging device configured to support medical containers, the packaging device comprising a first stage of supporting units configured to support a first plurality of medical containers in a first plane, a second stage of supporting units configured to support a second plurality of medical containers in a second plane parallel to said first plane, the first plane and the second plane being spaced apart from each other so that the distal ends of the first plurality of medical containers extend between medical containers of the second plurality of medical containers, and the supporting units of the first and second stages being configured so that the medical containers of the first and second pluralities of medical containers are oriented in a same direction, wherein the first stage of supporting units is formed by a first plate-shaped nest and the second stage of supporting units is formed by a second plate-shaped nest, wherein the packaging device comprises a strut element removably attached to the first and second stages of supporting units so as to fix together the first and second stages of supporting units.

2. The packaging device according to claim 1, wherein the supporting units of the first stage and the supporting units of the second stage are configured so that the first plurality of medical containers and the second plurality of medical containers are arranged in staggered rows relative to each other.

3. The packaging device according to claim 1, wherein the first stage of supporting units is configured to support a proximal end of the first plurality of medical containers and wherein the second stage of supporting units comprises a lateral blocking surface configured to prevent radial movement of the distal ends of the first plurality of medical containers.

4. The packaging device according to claim 1, wherein the first stage of supporting units comprises a maintaining surface configured to prevent the second plurality of medical containers from leaving the second stage of supporting units.

5. The packaging device according to claim 1, wherein the supporting units of the first and second stages respectively delimit a first aperture and a second aperture, the first aperture being configured to receive one medical container of the first plurality of medical containers and the second aperture being configured to receive one medical container of the second plurality of medical containers.

6. The packaging device according to claim 1, wherein the supporting units of the first and second stages respectively comprise at least one first axial stop and at least one second axial stop, the at least one first axial stop being configured to support a flange of a medical container of the first plurality of medical containers, and the at least one second axial stop being configured to support a flange of a medical container of the second plurality of medical containers.

7. The packaging device according to claim 1, wherein the supporting units of the first and second stages respectively comprise first and second guiding conduits configured to prevent radial movements of the first and second pluralities of medical containers.

8. The packaging device according to claim 7, wherein at least one of the first and second guiding conduits protrude from a bottom face of at least one of the first and second stages.

9. The packaging device according to claim 7, wherein at least one of the first and second guiding conduits each delimit at least one slit.

10. The packaging device according to claim 1, wherein the second stage comprises openings configured to receive the distal ends of the first plurality of medical containers, and slanted walls configured to guide the distal ends inside the openings.

11. The packaging device according to claim 1, wherein the packaging device comprises a housing containing the first and second stages of supporting units, said housing delimiting an opening configured to allow insertion or removal of the first and second stages together inside or outside the housing.

12. The packaging device according to claim 1, wherein the packaging device comprises keyed elements configured to allow a single predetermined positioning of the stages relative to each other.

13. A method for removing the pluralities of medical containers from the packaging device according to claim 1, comprising the step of removing the first stage of supporting units together with the second stage of supporting units.

14. The method according to claim 13, further comprising separating the first and second stages of supporting units from each other.

15. The method according to claim 14, wherein separating the first and second stages of supporting units from each other comprises removal of the strut element.

* * * * *